(12) United States Patent
Schoevaart et al.

(10) Patent No.: US 8,835,143 B2
(45) Date of Patent: Sep. 16, 2014

(54) METHOD FOR PREPARING HYBRID CROSS-LINKED ENZYME-SILICA AGGREGATES

(75) Inventors: Willem Robert Klaas Schoevaart, Delft (NL); Lukas Michael Van Langen, Delft (NL); Ronald Tako Marinus van Den Dool, Culemborg (NL); Johannes Wilhelmus Leonardus Boumans, Ouderkerk aan de Amstel (NL)

(73) Assignee: Clea Technologies BV, Delft (NL)

( * ) Notice: Subject to any disclaimer, the term of this patent is extended or adjusted under 35 U.S.C. 154(b) by 527 days.

(21) Appl. No.: 13/161,967

(22) Filed: Jun. 16, 2011

(65) Prior Publication Data
US 2012/0149082 A1 Jun. 14, 2012

Related U.S. Application Data

(63) Continuation-in-part of application No. 11/577,947, filed as application No. PCT/NL2005/000767 on Oct. 27, 2005, now abandoned.

(30) Foreign Application Priority Data

Oct. 28, 2004 (NL) ...................... 1027360

(51) Int. Cl.
| | |
|---|---|
| C12N 11/14 | (2006.01) |
| C12N 11/02 | (2006.01) |
| C12N 11/00 | (2006.01) |
| C12N 9/20 | (2006.01) |
| C12N 9/96 | (2006.01) |
| C12N 9/84 | (2006.01) |
| C12N 9/02 | (2006.01) |

(52) U.S. Cl.
CPC .. *C12N 9/96* (2013.01); *C12N 9/20* (2013.01); *C12Y 110/03002* (2013.01); *C12N 9/84* (2013.01); *C12Y 305/01011* (2013.01); *C12N 9/0061* (2013.01)
USPC ............................ 435/176; 435/177; 435/174

(58) Field of Classification Search
None
See application file for complete search history.

(56) References Cited

U.S. PATENT DOCUMENTS

| | | | |
|---|---|---|---|
| 3,868,303 | A | 2/1975 | Tsumura et al. |
| 5,002,884 | A | 3/1991 | Kobayashi et al. |
| 5,405,766 | A | 4/1995 | Kallury et al. |
| 5,437,993 | A | 8/1995 | Visuri |

FOREIGN PATENT DOCUMENTS

| | | |
|---|---|---|
| EP | 1088887 | 4/2001 |
| EP | 1418231 | 5/2004 |
| WO | 99/12959 | 3/1999 |

OTHER PUBLICATIONS

Vuolanto, Antti, "Cross-Linked Protein Crystal Technology in Bioseparation and Biocatalytic Applications", Aug. 20, 2004, Helsinki University of Technology, Espoo, Finland, pp. 10-13.
Lopez-Serrano P. et al., "Cross-Linked Enzyme Aggregates with Enhanced Activity: Application to Lipases", Biotechnology Letters, Kew, Surrey, Great Britain, vol. 24, No. 16, Aug. 2002, pp. 1379-1383.
Schoevaart R. et al., "Preparation, Optimization, and Structures of Cross-Linked Enzyme Aggregates (CLEAs)", Biotechnology and Bioengineering, vol. 87, No. 6, Sep. 20, 2004, pp. 754-762.
Poznansky, Mark J., "Soluble Enzyme-Albumin Conjugates: New Possibilities for Enzyme Replacement Therapy", Methods in Enzymology, vol. 137, No. D, 1988, pp. 566-574.
Written Opinion of the International Searching Authority for PCT/NL2005/000767 issued by the European Patent Office dated Aug. 28, 2006.

*Primary Examiner* — David M Naff
(74) *Attorney, Agent, or Firm* — Troutman Sanders LLP; Ryan A. Schneider; Troy S. Kleckley

(57) ABSTRACT

The invention relates to a method for the preparation of hybrid cross-linked enzyme-silica aggregates including the steps of taking up enzyme molecules in a solvent, precipitating the enzyme molecules using a precipitation agent, and adding an alkoxysilane and crosslinking the mixture of alkoxysilane and precipitated enzyme aggregates, using a crosslinking agent comprising an aldehyde, to obtain hybrid crosslinked enzyme-silica aggregates.

14 Claims, No Drawings

METHOD FOR PREPARING HYBRID CROSS-LINKED ENZYME-SILICA AGGREGATES

CROSS-REFERENCE TO RELATED APPLICATIONS

This application is a continuation-in-part of U.S. application Ser. No. 11/577,947, filed 21 Aug. 2007, now abandoned, which application is a US National Stage of International Application No. PCT/NL05/00767, filed 27 Oct. 2005, which claims the benefit of NL 1027360 filed 28 Oct. 2004, all herein fully incorporated by reference.

BACKGROUND OF THE INVENTION

1. Field of the Invention

The present invention relates to a method for the preparation of cross-linked enzyme aggregates, more specifically to a method for the preparation of hybrid cross-linked enzyme-silica aggregates.

2. Description of Related Art

Methods for the preparation of cross-linked enzyme aggregates are known in the art. Such a method is, for example, described in EP 1,088,887 A1, and discloses the production of crosslinked enzyme aggregates by precipitating an enzyme from solution with a precipitating agent whereby aggregates are formed, and crosslinking the precipitated enzyme with a crosslinking agent. It is indicated that, during aggregation, a carrier may be present. Any information about the specific nature of a suitable carrier, and at which stage the carrier should be added, is missing in this reference.

The possibilities of varying properties afforded by such known methods is nevertheless limited, and consequently such methods often result in cross-linked enzyme aggregates (called CLEAs) with properties, in particular activity and colloidal behavior, that are not optimal for the ultimate purpose of the cross-linked enzyme aggregates.

Further, methods for the immobilization of enzymes on a carrier are also known, for example in U.S. Pat. No. 5,002,884 to Kobayashi et al., and U.S. Pat. No. 5,405,766 to Kallury et al. Kobayashi and Kallury teach that enzymes can be immobilized on silica, as a carrier, the surface of which has been modified by pretreatment with an alkoxysilane. The enzyme is thus anchored onto the modified carrier surface. The enzyme loading of the obtained aggregates is rather low.

BRIEF SUMMARY OF THE INVENTION

Briefly described, in a preferred form, the present invention is a method for the preparation of novel cross-linked enzyme-silica aggregates, which surprisingly shows much higher enzyme loadings than obtainable in a product, produced by immobilization of an enzyme, as cross-linked enzyme aggregates or otherwise on a preformed/pretreated silica support.

The present enzyme-silica aggregates are more specifically hybrid cross-linked enzyme-silica aggregates, which are prepared by a method comprising:
  i. taking up the enzyme molecules in a solvent;
  i. precipitating the enzyme molecules using a precipitation agent; and
  iii. adding an alkoxysilane and crosslinking the mixture of alkoxysilane and precipitated enzyme aggregates, using a crosslinking agent comprising an aldehyde, such as glutaraldehyde, to obtain hybrid crosslinked enzyme-silica aggregates.

In a variety of exemplary embodiments, one or more of the following can be incorporated into the method: the crosslinking agent can further comprise an amine compound. The alkoxysilane can be selected from the group consisting of $(MeO)_4Si$, $(EtO)_4Si$, $Me(MeO)_3Si$ and Propyl $(MeO)_3Si$. A reduction agent can be added in step (iii), and the reduction agent can comprise $NaCNBH_3$ or $NaBH_4$. In step (iii) ammonia can be used as the amine compound. In step (iii) a di- or polyamine can be used as the amine compound. The amine compound in step (iii) can be derived from the precipitation agent. The precipitation agent can be an ammonium compound, the amine compound can be ammonia, and the method can be performed at a pH of between approximately 8-9.5. The ammonium compound can be ammonium sulfate. Step (i) can be carried out by the addition of an aldehyde compound. Step (i) can be carried out by the addition of an oxidant. The oxidant can be selected from the group consisting of periodates of alkaline earth metals. The enzyme can be a protein. The enzyme molecules can be selected from the group consisting of laccase, lipase, protease, esterase, oxynitrilase, nitrilase, aminoacylase, penicillin acylase, lyase, oxidase and reductase molecules.

These and other objects, features and advantages of the present invention will become more apparent upon reading the following specification in conjunction with the accompanying examples.

DETAILED DESCRIPTION OF PREFERRED EMBODIMENTS

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

It was surprisingly found that the thus obtained hybrid crosslinked enzyme-silica aggregates show much higher enzyme loadings than found in enzyme-silica aggregates obtained by immobilization on a preformed/pretreated silica support. Moreover, the obtained aggregates are mechanically more robust, and have larger particle sizes.

Although Applicant does not wish to be bound by any theory, it is assumed that the crosslinking of the enzyme aggregates in the presence of the polymerizing alkoxysilane molecules results, according to the invention, in an intimate mixed product, having a structure of random distribution of enzyme aggregates and silica in the aggregate particles. It is in this respect observed that also in the field of polymer production, the order in which the components are added, determines the specifications of the obtained end product and thus the characteristics thereof. This random structure is different from a structure in which only a layer of molecules has been bound (by immobilization) onto the surface of a carrier such as silica.

The crosslinking agent can comprise two components, namely an aldehyde component, such as glutaraldehyde, and an amine component to be added separately, which together can be applied in many different combinations. The aldehyde component may be a di- or polyaldehyde.

By modifying the structure of the alkoxysilane, the hydrophobicity/hydrophilicity of the present hybrid crosslinked enzyme-silica aggregates can be, further, fine-tuned.

Such aldehydes are shown to be cheap and effective agents for the generation of aldehyde groups on an enzyme molecule.

In accordance with a preferred embodiment of the present invention, step i. in the method according to the invention is carried out by the addition of a suitable oxidant.

Moreover, the oxidant is preferably selected from the group of periodates of alkaline-earth metals, wherein sodiumperiodate ($NaIO_4$).

Carrying out step i. of the method according to the invention (the generation of aldehyde groups on the enzyme molecules), by adding a suitable oxidant such as $NaIO_4$, has the advantage that aldehyde groups are generated on specific sites on the enzyme and that generally the enzymatic activity is preserved. Moreover, any salts that may be formed can simply be washed away during an optional wash step.

It is also preferred to add a reducing agent in step iii.

The addition of a reducing agent causes free aldehyde groups of the enzyme to bond with the added amines.

The addition of a reducing agent in step iii. of the method according to the invention has the advantage that cross-linking occurs in a few minutes so that, compared with other methods, the preparation time is shorter. In addition, aldehydes that have not reacted with an amine are inactivated, preventing them from reacting at a later stage. This latter aspect is important because it prevents the particle size of the cross-linked enzyme aggregates from becoming larger than 10 to 50 micrometers. Particles becoming too large have an adverse effect on the activity. Besides a reduction agent particle increase can be avoided by the addition of alkoxysilanes. Furthermore, by choosing a more hydrophobic or a more hydrophilic silicate the hydrophobicity of the CLEA can be controlled.

The reducing agent is preferably selected from the group of $NaCNBH_3$ or $NaBH_4$.

These reducing agents were shown to be especially suitable.

The alkoxysilanes are preferably selected from the group of $(MeO)_4Si$, $(EtO)_4Si$, $Me(MeO)_3Si$ and Propyl $(MeO)_3Si$.

In step iii. of the method according to the present invention it is preferred to use ammonia as amine compound.

Until now it was common practice only to consider di- and polyamine compounds as cross-linking agents for cross-linked enzyme aggregates. However, the inventors have now found that using ammonia as cross-linking agent provides cross-linked enzyme aggregates with favorable properties. When using ammonia as amine compound, the cross-linked enzyme aggregates that are obtained are generally not colored. The particles are uniform, and the small particles that are formed can be instantly resuspended in water without extra mechanical treatment. This yields good activity.

It is further preferred to use a diamine as amine compound in step iii. of the method.

Until now it was common practice to associate the length of the diamine as cross-linking agent with the activity and the cross-linked enzyme particles obtained thereby.

Surprisingly, it has now been found that with the method of the invention aldehyde groups are generated, without the occurrence of cross-linking, so that in order to obtain particular physical properties of the cross-linked enzyme aggregates the di- or polyamide can be specifically selected.

For example, the introduction of acidic groups (e.g. using the amino acid lysine) gives the cross-linked enzyme aggregate a negative charge in a basic environment, and the introduction of basic groups (e.g. using polyethylenediamines such as pentaethylenehexamine) gives the cross-linked enzyme aggregate a positive charge in an acidic environment. These treatments result in different colloidal behavior. By applying the modification that is the most favorable for the enzyme, the activity can be maintained or increased. It is also possible for apolar groups (e.g. using xylenediamine, polyxylenediamine, 1,3-propanediamine, hexanediamine) or polar groups (e.g. 1,3-diamino-2-propanol) to be incorporated, depending on the solvent that is used in the intended application. The amine may also be obtained from the protein itself, in the form of amine-comprising side groups of amino acids, such as lysine.

It is further preferred for the amine compound in step ii. of the method according to the present invention to be derived from the precipitation agent of step i.

This has the advantage that in order to perform step iii. it is not necessary to separately add an amine compound so that fewer operations are necessary and, due to the higher amine concentration, fewer reactive amines are needed with all the consequential time and cost savings.

The precipitation agent is preferably an ammonium compound and the amine compound ammonia, the method being performed at a between approximately pH of 8-9.5. When using di- or polyamines it is preferred not to use ammonium salt but polyethylene glycol or another amine-free solvent.

It is still more preferred for the ammonium compound to be ammonium sulfate. When using ammonium sulfate and glutaraldehyde no spontaneous cross-linking takes place if the pH is kept between approximately 8 and 9.5. At a lower pH, spontaneous cross-linking does occur before the reduction step can take place so that cross-linked aggregates are obtained having very strongly deviating properties such as discoloring and large particles.

When using di- or polyamines the pH may be varied between approximately 1 and 14, preferably between approximately 4 and 10 and most optimally between approximately 6 and 8.

It has further been found that the enzyme molecules in the method according to the present invention can be precipitated with a suitable precipitation agent (step i.) preceding the generation of aldehyde groups on the enzyme molecules (step ii.).

This aspect of the method may be employed advantageously, for example, when $NaIO_4$ is used to introduce aldehyde groups on the protein. $NaIO_4$ dissolves very well in aqueous solvents (containing the enzymes before precipitation), whereas it dissolves poorly in the usual precipitation agents. This reduces its activity after aggregation and avoids disruption of further steps in the process.

The particle size of the cross-linked enzyme aggregates obtained using the method according to the present invention may in some cases be too small for filtering with the aid of, for example, conventional glass filters.

It is therefore advantageous if the possibility exists to enlarge the particle size of the cross-linked enzyme aggregates.

To this end the method according to the present invention is characterized in a preferred embodiment by the addition in step i. of a carrier material.

The carrier material is preferably silica, Sepabeads® or another known enzyme carrier.

According to the prior art, enzymes and cross-linked enzyme aggregates are generally washed with a buffer solution. It is generally accepted that washing with a buffer is best for the quality of the aggregates.

In contrast, it has now been found that it is advantageous if after step iii. of the method according to the present invention, the cross-linked enzyme aggregates are washed with demineralized water, followed by a drying step.

Salts and other substances in solution are thus effectively washed away, resulting in increased activity in organic media and in ionic liquids.

Subsequently, it is preferred for the drying step to be carried out by treatment with an organic solvent, preferably selected from the group of water-miscible solvents such as acetone, alcohols and ionic liquids. The water-miscible solvent may optionally be washed away with a more volatile solvent (such as diethyl ether) in order to expedite the drying process.

It has been shown that the activity in organic media and ionic liquids of cross-linked enzyme aggregates prepared by using the method according to the present invention is improved. Acetone, water-miscible ethers, alcohols and ionic liquids have been found to be inexpensive and effective solvents.

The organic solvent may subsequently be removed by the addition of ether, followed by evaporation.

The addition of ether followed by evaporation dries very efficiently. Optionally, a known amount of water may be added to the cross-linked aggregate if this appears to enhance the activity. This may, for example, be carried out by adding acetone to a known percentage of water and subsequently removing the acetone with ether. A small amount of water in the cross-linked aggregate may result in enhanced activity, if the medium in which the cross-linked aggregate is ultimately used is a water-free medium.

In another aspect, the present invention relates to enzyme aggregates that can be obtained in accordance with the methods of the present invention.

Compared with aggregates prepared in accordance with prior art methods, the activity and colloidal behavior of these aggregates is improved.

Favorable results were obtained when the enzyme molecules were selected from the group of laccase molecules and lipase molecules, but the method according to the present invention may also be applied to other enzymes such as proteases, esterases, oxynitrilase, nitrilase, aminoacylase, penicillin acylase, oxidases, and reductases. Especially, lipases and esterases are often used under "dry" conditions, so that drying is very important. Too much water can cause a disruption in the reaction catalyzed by the enzyme.

Another favorable feature of cross-linked enzyme aggregates, apart from an enhanced activity, is an improvement of the stability. An important technical limitation of the use of the enzyme laccase for the oxidation of carbohydrates like starch (as known from, for example, WO 0050621) is the fact that during the reaction, the enzyme laccase is also oxidized by the additive 2,2,6,6-tetramethyl-1-piperidinyloxy (TEMPO). As a consequence, the enzyme becomes inactivated after a period of time. This means that during the oxidation process, fresh laccase must be added continuously. For economical reasons, this process can hardly compete with the present-day technology, despite the obvious environmental advantages.

By making a cross-linked aggregate from laccase, the enzyme is better protected against oxidation. The life span during the oxidation of starch is extended, so that the process becomes cost-effective.

Because a free enzyme is unable to penetrate into the cross-linked enzyme aggregate, which is only accessible to smaller molecules, enzymes are in the cross-linked, aggregated condition protected against attack from degrading enzymes such as proteases. This advantage is shown, for example, in the case of laccase enzymes. Although the dissolved enzyme composition shows protease as well as laccase activity, no protease activity can be detected in the cross-linked enzyme aggregate. Compared to the free laccase composition, the stability of the laccase enzyme molecules is much improved in cross-linked enzyme aggregates. An extra purification step of the laccase enzyme molecules is thus rendered superfluous.

For the application of the laccase in the oxidation of starch, this advantage is exhibited in another way. Apart from laccase and protease activity, the dissolved enzyme composition also exhibits amylase activity. Amylase degrades starch into smaller fragments. This is undesirable because smaller starch fragments oxidized by laccase have much poorer properties than starch that is not degraded by amylase and oxidized by laccase. In the cross-linked aggregated form the amylase activity—similar to the protease activity—was shown to be greatly reduced. Thus starch is also too large to penetrate into the cross-linked enzyme aggregate, which normally results in hydrolysis into smaller fragments, leading to undesirable product characteristics. Here also, an extra purification step is superfluous.

The invention will now be elucidated by way of the following, non-limiting examples.

EXAMPLES

Example 1

Laccase Activity

Laccase (*Trametes versicolor*, Wacker Chemie) activity was measured by dissolving an amount of laccase enzyme in 40 mM sodium acetate buffer pH 4.5. 100 mg 2,2-azinobis (3-ethylbenzthiazoline-6-sulphonate) (ABTS) was dissolved in 20 ml of the same buffer and 200 µl of this solution was mixed with 800 µl of the laccase solution and incubated at 25° C. The extinction change at 420 nm was used to determine the laccase activity. One unit of activity (U) is defined as the amount of enzyme inducing a change in extinction of 0.027 $dE^{420}$ per minute in a reaction volume of 1 ml.

Example 2

Preparation of the Nitrosonium Salt of 2,2,6,6-Tetramethyl-1-Piperidinyloxy (TEMPO) Using Laccase A solution of TEMPO-nitrosonium ion was prepared as follows using laccase: 6.9 g TEMPO was dissolved in 1 liter demineralized water. 200 mg laccase from *Trametes versicolor* (Wacker) was suspended in 20 ml demineralized water. After stirring the enzyme solution for 10 minutes, the supernatant (centrifugation 5 minutes at 1500×g) was desalted using a P6 column. The desalted material was added to the TEMPO solution. After approximately 150 minutes under pH stat conditions at pH 5, room temperature, while aerating using an aerator, 91% of the TEMPO was converted into nitrosonium, as was apparent from the consumption of 100.8 ml HCL (0.4 N) and a color shift from yellow to a more orange tint (the ratio E480/E430 increased from approximately 0.3 to 1.4).

Example 3

Diamine Selection and Optimization 25 mg laccase (*Trametes versicolor*, Wacker Chemie) was dissolved in 1 ml 100 mM sodium acetate buffer pH 4.5 at 4° C. After centrifugation, 0.9 g polyethylene glycol (8000 k), was added to the supernatant at room temperature. After stirring for 30 minutes, chilled (4° C.) glutaraldehyde (25% solution) was added to a final concentration of ten times (50-150 mM) that of the diamine. The solution thus obtained was stirred for 5 minutes at room temperature. Subsequently, a selected diamine (as 100 mM solution, pH 4.5) was added all at once, having different final concentrations (5-15 mM). The mixture was stirred slowly for 3 hours at room temperature.

TABLE 1

Diamine selection and optimisation

| | mM diamine | | mM glutaral- dehyde | % CLEA* activity yield | U/mg | appearance of the CLEA* suspension |
|---|---|---|---|---|---|---|
| 1 | 5 | PDA | 50 | 45 | 3.89 | flocculent, precipitates quickly |
| 2 | 10 | PDA | 100 | 39 | 3.38 | |
| 3 | 15 | PDA | 150 | 33 | 2.88 | |
| 4 | 5 | HMDA | 50 | 63 | 4.14 | powdery, precipitates quickly |
| 5 | 10 | HMDA | 100 | 47 | 4.03 | |
| 6 | 15 | HMDA | 150 | 36 | 3.09 | |
| 7 | 5 | PEHA | 50 | 48 | 4.20 | flocculent, precipitates very slowly |
| 8 | 10 | PEHA | 100 | 34 | 3.94 | |
| 9 | 15 | PEHA | 150 | 30 | 2.55 | |
| 10 | 5 | PXDA | 50 | 45 | 3.87 | large particles |
| 11 | 10 | PXDA | 100 | 31 | 2.67 | |
| 12 | 15 | PXDA | 150 | 30 | 2.56 | |

*CLEA = cross-linked enzyme aggregate
PDA = 1,3-propanediamine;
HMDA = 1,6-hexamethylenediamine;
PEHA = pentaethylenehexamine;
PXDA = polyxylylenediamine

TABLE 2

Activity of cross-linked enzyme aggregates after washing and resuspension with pentaethylenehexamine as diamine

| | mM PEHA | % CLEA* activity yield | U/mg |
|---|---|---|---|
| 1 | 2.5 | 32 | 2.79 |
| 2 | 5 | 31 | 4.25 |
| 3 | 7.5 | 32 | 3.76 |
| 4 | 10 | 38 | 3.95 |
| 5 | 12.5 | 37 | 3.16 |
| 6 | 15 | 37 | 2.50 |

*CLEA = cross-linked enzyme aggregate

Example 4

Preparation I of Cross-Linked Laccase Enzyme Aggregate (Glutaraldehyde and Pentaethylenediamine)

1 g laccase (*Trametes versicolor*, Wacker Chemie) was dissolved in 40 ml 100 mM sodium acetate buffer pH 4.5 at 4° C. After centrifugation 36 g polyethylene glycol (8000 k) was added to the supernatant at room temperature. After stifling for 30 minutes, 2.873 ml chilled (4° C.) glutaraldehyde (25% solution) was added dropwise. The obtained solution was stirred for 5 minutes at room temperature. Subsequently 7.4 ml pentaethylenediamine (PEHA) (as 100 mM solution, pH 4.5) was added all at once. The mixture was stirred slowly for 3 hours at room temperature. Subsequently, 200 ml water was added and the cross-linked enzyme aggregate was centrifuged. The pellet was resuspended in 9 ml 100 mM sodium acetate buffer pH 4.5 containing 10% polyethylene glycol (8000 k), and frozen.

Example 5

Working Up the Cross-Linked Enzyme Aggregates by Means of a Drying Step

The cross-linked enzyme aggregate was prepared as in Example 4. On completion of the cross-linking, the crosslinked enzyme aggregate suspension was washed 3× (centrifuged and decanted) with a same volume of demineralized water to wash out all the soluble components. The pellet was then resuspended in acetone, another water soluble solvent would also be suitable, centrifuged and resuspended in diethylether (a comparable solvent would also be suitable). After centrifugation, the cross-linked enzyme aggregate was free of salts or other components. It was storable in the ether as suspension or the ether could be evaporated to isolate the cross-linked enzyme aggregate in the form of dry powder.

Example 6

Preparation II of Cross-Linked Laccase Enzyme Aggregate

Periodate Oxidation and Pentaethylenediamine 1 g of laccase (*Trametes versicolor*, Wacker Chemie) was dissolved in 10 ml 100 mM sodium acetate buffer pH 4.5 at 4° C. After centrifugation, 10 ml 100 mM sodium metaperiodate was added to the supernatant. After incubating for 1 hour at 4° C., 18 g polyethylene glycol (8000 k) was added to the supernatant at room temperature. After stifling for 30 minutes, 3.7 ml pentaethylenediamine (PEHA) (as 100 mM solution, pH 4.5) was added all at once. The obtained solution was stirred for 2 hours at room temperature. Then, 4 ml chilled (4° C.) sodium cyanoborohydride (100 mM solution) was added.

The mixture was slowly stirred for 1 hour at room temperature. Then 200 ml water was added and the cross-linked enzyme aggregate was centrifuged. The pellet was resuspended in 10 ml 100 mM sodium acetate buffer pH 4.5 containing 10% polyethylene glycol (8000 k), and frozen.

Example 7

Preparation of Cross-Linked Laccase Enzyme Aggregate III

Periodate Oxidation and Ammonia 1 g laccase (*Trametes versicolor*, Wacker Chemie) was dissolved in 10 ml 100 mM sodium acetate buffer pH 4.5, at 4° C. After centrifugation, 10 ml 100 nM sodium metaperiodate was added to the supernatant. After incubation for 1 hour at 4° C., 10 g ammonium sulfate was added to the supernatant at room temperature and the pH was adjusted to 8.5. The mixture was then stirred for 2 hours at room temperature at pH 8.5. Then 4 ml chilled (4° C.) sodium cyanoborohydride (100 mM solution) was added. The mixture was stirred slowly for 1 hour at room temperature. Then 200 ml water was added and the cross-linked enzyme aggregate was centrifuged. The pellet was resuspended in 10 ml 100 mM sodium acetate buffer pH 4.5 containing 10% polyethylene glycol (8000 k) and, frozen.

Example 8

The Stability of Laccase in the Presence of the Nitrosonium Salt of TEMPO

A solution of 0.5 mg/ml laccase in 0.2 M succinate buffer pH 6 was prepared and the nitrosonium salt of TEMPO was added to give a final concentration of 32 mM. The solution was incubated and the residual enzyme activity was determined. From the relationship between the activity and time, the half-life of laccase in the presence of the nitrosonium salt of TEMPO was calculated. The same experiment was conducted with the cross-linked enzyme aggregate of Example 4 (preparation I of cross-linked laccase enzyme aggregate) in the same buffer and in the presence of 32 mM of the nitrosonium salt of TEMPO.

TABLE 3

Half-life of cross-linked laccase enzyme aggregates

| Enzyme | Half-life in the presence of the nitrosonium salt of TEMPO |
|---|---|
| Free Laccase | 15 minutes |
| Laccase-CLEA* Example 4 | 116 minutes |

*CLEA = cross-linked enzyme aggregates

Example 9

The Stability of Cross-Linked Laccase Enzyme Aggregate at 55° C.

A solution of 0.5 mg/ml laccase (*T. versicolor*) in 40 mM sodium acetate buffer pH 4.5 and a solution of 0.5 mg/ml cross-linked enzyme aggregate from Example 4 in the same buffer was incubated at 55° C. and the activity was determined at regular intervals. From the activity decrease in time it was possible to determine the half-life under these conditions. The half-life of laccase was shown to be approximately 11 hours, and that of the cross-linked enzyme aggregate from Example 4 approximately 40 hours.

Example 10

Oxidation of Starch

Starch solutions were prepared by gelling Lintner potato starch (Sigma S-2630) in water. For each experiment a solution of 16 g gelled starch in 800 ml 0.1 M succinate buffer pH 5.6 was prepared. To this solution 3.2 g TEMPO was added. (Under certain circumstances, TEMPO forms a precipitate with starch, which dissolves during the process). In each experiment, 30% of the total amount of enzyme units was added at the beginning of the reaction. During the first 6 hours of the reaction, the remaining 70% of the enzyme units was added in 6 aliquots per hour. The reaction temperature was 37° C. The pH was kept constant using a pH stat. The conversion of starch was measured by means of online analysis of the hydroxide consumption. The degree of conversion is defined as the percentage of C6-hydroxyl groups converted to carboxylic acid groups.

TABLE 4

Stability of cross-linked enzyme aggregates from Example 4.

| Enzyme | Total of units used | Degree of conversion after 24 hours |
|---|---|---|
| Laccase | 2000 | 61% |
| Laccase | 1700 | 51% |
| Cross-linked enzyme aggregate from Example 4 | 1377 | 64% |

The results show that considerably fewer units are needed when the cross-linked enzyme aggregate from Example 4 is used instead of soluble laccase.

Example 11

Preparation I of Cross-Linked Lipase Enzyme Aggregate

Glutaraldehyde with Reduction

An amount of 0.45 gram potassium hydrogen phosphate was added to 150 ml of lipase (CaLB, Novozyme 525F) and the pH was adjusted to 7.3 with diluted phosphoric acid. Then 135 g polyethylene glycol (8000 k) was added and the mixture stirred for 30 minutes at room temperature, after which 10.85 ml glutaraldehyde (25% solution in water) was added. After stirring for 3 hours at room temperature, 28.5 ml chilled (4° C.) sodium cyanoborohydride (100 mM solution) was added. The mixture was slowly stirred for 30 minutes at room temperature. Then 285 ml water was added and the mixture was stirred for another 30 minutes. Then the cross-linked enzyme aggregate was centrifuged. The pellet was washed thrice with 400 ml demineralized water (centrifuging, decanting), once with 300 ml acetone, once with 150 ml acetone and once with 150 ml diethylether. After evaporation of the ether, the pellet was obtained as dry powder.

TABLE 5

Diamine selection for periodate-oxidised *Candida antarctica* lipase B.

| Pellet structure | Diamine (10 mM) | % Yield CLEA* |
|---|---|---|
| thin | EDA | 53 |
| thin | P1,2DA | 46 |
| thin | PDA | 64 |
| thin | HMDA | 85 |
| thin | XDA | 91 |
| flocculent | PXDA | 94 |
| very flocculent | PEHA | 91 |
| thin | Lysine | 71 |
| thin | Lysine ethylester | 62 |

*CLEA = cross-linked enzyme aggregate
EDA = 1,2 diamino ethane; P1,2DA = 1,2-propanediamine PDA = 1,3-propanediamine; HMDA = 1,6-hexamethylenediamine; XDA = xylenediamine; PXDA = polyxylylenediamine; PEHA = pentaethylenehexamine;

TABLE 6

Diamine optimisation for periodate-oxidised *Candida antarctica* lipase B.

| Diamine | Concentration mM | % Yield CLEA* |
|---|---|---|
| HMDA | 5 | 76 |
| HMDA | 10 | 82 |
| HMDA | 15 | 83 |
| PXDA | 5 | 82 |
| PXDA | 10 | 85 |
| PXDA | 15 | 79 |
| PEHA | 5 | 80 |
| PEHA | 10 | 62 |
| PEHA | 15 | 67 |

*CLEA = cross-linked enzyme aggregate

Example 12

Lipase Cross-Linked Enzyme Aggregate Preparation II

Periodate Oxidation and Polyxylylenediamine

An amount of 150 ml 100 mM sodium metaperiodate was added to 150 ml lipase (CaLB, Novozyme 525F) and the mixture was kept for 1 hour at room temperature. Subsequently 1.3 grams of potassium hydrogen phosphate was added and the pH was adjusted to 7.8 with diluted phosphoric acid. Then 270 g polyethylene glycol (8000 k) was added and the mixture was stirred for 5 minutes at room temperature, after which 57 ml polyxylylenediamine (100 mM, pH 7.8) solution was added all at once. After 10 minutes, 57 ml chilled (4° C.) sodium cyanoborohydride (100 mM solution) was added.

The mixture was slowly stirred for 1 hour at room temperature. After that, 285 ml water was added and stirred for 1 more hour. Then the cross-linked enzyme aggregate was centrifuged. The pellet was washed thrice with 400 ml demineralized water (centrifuging, decanting), once with 300 ml acetone, once with 150 ml acetone and once with 150 ml diethylether. After evaporating the ether, the pellet was obtained in the form of dry powder.

TABLE 7

Activity of *Candida antarctica* lipase B formulations in organic media.

| | Hydrolytic activity$^a$ | Deesterification$^b$ |
|---|---|---|
| Free lipase | 22000 | — |
| Novozyme 435 | 7300 | 250 |
| CLEA-example K not reduced | 3000 | 11 |
| CLEA-example K reduced | 38000 | 50 |
| CLEA-example L | 31000 | 1500 |

$^a$Tributyrin units/gram: 5 vol. % tributyrine in 40 mM Tris buffer; pH 7.5; 40° C.
$^b$Phenylethylamine 41 mM; n-butyl methoxyacetate 34 mM; 12 mg/ml, Mol. sieve 4 A, 40° C.

Example 13

Lipolase Cross-Linked Enzyme Aggregate Preparation

Periodate Oxidation and Polyxylylenediamine

An amount of 100 ml 300 mM sodium metaperiodate was added to 100 ml lipolase (*Thermomyces Lanuginosa*, Novozyme Lipolase® 100 L) and the mixture was kept for 1 hour at room temperature. Subsequently, 0.6 grams of potassium hydrogen phosphate was added and the pH was adjusted to 6.6 with diluted phosphoric acid. Then 160 g polyethylene glycol (8000 k) was added and the mixture was stirred for 15 minutes at room temperature, after which 35 ml polyxylylenediamine (100 mM) solution was added all at once. After 10 minutes, 35 ml chilled (4° C.) sodium cyanoborohydride (100 mM solution) was added. The mixture was slowly stirred for 1 hour at room temperature. After that, 250 ml water was added and stirred for 1 more hour. Then the cross-linked enzyme aggregate was centrifuged. The pellet was washed thrice with 400 ml demineralized water (centrifuging, decanting), once with 300 ml acetone, once with 150 ml acetone and once with 150 ml diethylether. After evaporating the ether, the pellet was obtained in the form of dry powder. The yield was 3.95 g with an activity of 189000 tributyrin units per gram.

Example 14

Lipolase Cross-Linked Enzyme Aggregate Preparation

Periodate Oxidation and Polyxylylenediamine with a Silica Coating

An amount of 100 ml 300 mM sodium metaperiodate was added to 100 ml lipolase (*Thermomyces Lanuginosa*, Novozyme Lipolase® 100 L) and the mixture was kept for 1 hour at room temperature. Subsequently, 0.6 grams of potassium hydrogen phosphate was added and the pH was adjusted to 6.6 with diluted phosphoric acid. Then 160 g polyethylene glycol (8000 k) was added and the mixture was stirred for 15 minutes at room temperature, after which 35 ml polyxylylenediamine (100 mM) solution was added all at once. After 10 minutes, 35 ml chilled (4° C.) sodium cyanoborohydride (100 mM solution) was added. The mixture was slowly stirred for 1 hour at room temperature. Then sodium fluoride was added (25 ml 1 M solution) and subsequent 10 ml of $(EtO)_4Si$. After stirring overnight, 250 ml water was added and the suspension was filtered over a P4 glass filter. The pellet was washed thrice with 400 ml demineralized water, once with 300 ml acetone, once with 150 ml acetone and once with 150 ml diethylether. After evaporating the ether, the pellet was obtained in the form of dry powder. The yield was 6 g with an activity of 650000 tributyrin units per gram.

Example 15

Cross-Linking of Enzyme Aggregates with the Addition of a Carrier

In order to obtain a good bond between the aggregate and the carrier, silica (Davisil 644, 100-200 mesh, 150 .ANG.) was pre-treated with 3-aminopropyltriethoxysilane (as described in WO 03/031610). This causes amino groups to be formed on the carrier which, as described, are able to react with the aldehyde groups on the enzyme. To 1 g of this pre-treated silica, 5 ml demineralized water and 12 ml of the periodate-treated and with polyethylene glycol aggregated enzyme (CaLB, Novozyme 525F) from Example 12 was added. It is also possible to add the silica before aggregation. After stifling for 15 minutes, 1.7 ml PXDA (100 mM) was added and the mixture stirred for 2 hours. Subsequently, it was reduced for 1 hour using 1.7 ml 100 mM $NaCNBH_3$. The thus obtained cross-linked enzyme aggregate was washed on a glass filter with water, acetone and ether. The activity of the solid (900 mg) in the tributyrine assay was 2400 units per gram. This corresponds with approximately 10% enzyme per gram of carrier material.

Example 16

Cross-Linking of Enzyme Aggregates with the Addition of a Carrier II

To 2.5 g of Sepabeads® FP serie, EC-EA300 (Resindion, Italy), 2 ml demineralized water and 2 ml of the periodate-treated CaLB from Example 12 was added. The pH was adjusted to 7.5. After shaking for 1 hour 15 ml 2-propanol was added and subsequently, it was reduced for 1 hour using 2 ml 100 mM $NaCNBH_3$. The thus obtained particles were washed on a glass filter with water, acetone and ether. The activity of the solid (900 mg) in the tributyrin assay was 3000 units per gram.

Example 17

Penicillin Acylase/Silica Hybrid Cross-Linked Enzyme Aggregates

To 150 ml of 2-propanol an amount of 50 ml of crude penicillin acylase solution (300 U/ml) was slowly added and the mixture was kept at room temperature for 30 minutes. Subsequently 2.5 ml glutaraldehyde (25% aq.) was added to the suspension followed by 5 ml $(MeO)_4Si$ and 1 ml NaF (1M solution). After stifling at room temperature for 3 hours the suspension was filtered over a P3 glass filter and washed three times with 200 ml water. Finally the cake was resuspended in 175 ml of phosphate buffer (25 mM, pH 8). This yielded 11550 units (66 U/ml) in a standard penicillin G hydrolysis assay (pH stat titration of the hydrolysis of 0.5 g. penicillin G potassium salt in 25 ml phosphate buffer (25 mM, pH 8) at 40 degrees C.).

Example 18

*Candida antarctica* Lipase A/Silica Hybrid CLEAs

To 5 liters of 2-propanol 2 liters *Candida Antarctica* lipase A solution (Novozym 735) was added and the mixture was stirred at room temperature for 30 minutes. Subsequently 66 ml of glutaraldehyde solution (25% aq.) was added. After stirring this suspension at room temperature for one hour sodium fluoride solution (35 ml, 1M) was added, followed by 200 ml $(EtO)_4Si$. After stirring overnight at room temperature this was filtered over a P3 glass filter and the cake washed three times with 5 L water and once with acetone. Afterwards the HCLEAs were resuspended in 2.5 L acetone for storage. This procedure yielded 202 gram dry weight in 2.5 L acetone with a total activity of 6.5 million tributyrin hydrolysis units.

What is claimed is:

1. A method for the preparation of hybrid cross-linked enzyme-silica aggregates comprising:
   i. taking up enzyme molecules in a water-containing solvent;
   ii. precipitating the enzyme molecules using a precipitation agent to produce precipitated enzyme aggregates; and
   iii. adding an alkoxysilane to the precipitated enzyme aggregates to produce a mixture of alkoxysilane and precipitated enzyme aggregates, and crosslinking the mixture using a crosslinking agent comprising an aldehyde, to obtain hybrid crosslinked enzyme-silica aggregates.

2. Method according to claim 1, the crosslinking agent further comprising an amine compound.

3. Method according to claim 1, wherein the alkoxysilane is selected from the group consisting of $(MeO)_4Si$, $(EtO)_4Si$, $Me(MeO)_3Si$ and Propyl $(MeO)_3Si$.

4. Method according to claim 2, wherein a reduction agent is added in step (iii) to promote the bonding of at least a portion of the aldehyde with at least a portion of the amine compound.

5. Method according to claim 4, wherein the reduction agent comprises one of $NaCNBH_3$ and $NaBH_4$.

6. Method according to claim 2, wherein the amine compound comprises ammonia.

7. Method according to claim 2, wherein the amine compound comprises a di- or polyamine.

8. Method according to claim 2, wherein the amine compound is derived from the precipitation agent.

9. Method according to claim 8, wherein the precipitation agent comprises an ammonium compound, wherein the amine compound comprises ammonia, and wherein the method is performed at a pH of between approximately 8-9.5.

10. Method according to claim 9, wherein the ammonium compound comprises ammonium sulfate.

11. Method according to claim 1, wherein in step (i) an oxidant is added.

12. Method according to claim 11, wherein the oxidant is selected from the group consisting of periodates of alkaline earth metals.

13. Method according to claim 1, wherein the enzyme comprises a protein.

14. Method according to claim 1, wherein the enzyme molecules are selected from the group consisting of laccase, lipase, protease, esterase, oxynitrilase, nitrilase, aminoacylase, penicillin acylase, lyase, oxidase and reductase molecules.

* * * * *